US008900551B2

(12) United States Patent
Lee et al.

(10) Patent No.: US 8,900,551 B2
(45) Date of Patent: *Dec. 2, 2014

(54) PEPTIDE WHICH PASSES THROUGH BLOOD-BRAIN BARRIER AND TARGETS APOPTOSIS OF NEURODEGENERATIVE BRAIN DISEASE SITE AND USES THEREOF

(75) Inventors: Byung-Heon Lee, Daegu (KR); In-San Kim, Daegu (KR); Jae-Sung Bae, Daegu (KR); Hee Kyoung Jin, Daegu (KR); Hyung Soo Han, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 157 days.

This patent is subject to a terminal disclaimer.

(21) Appl. No.: 13/469,729

(22) Filed: May 11, 2012

(65) Prior Publication Data
US 2012/0288447 A1 Nov. 15, 2012

Related U.S. Application Data

(63) Continuation of application No. PCT/KR2010/008000, filed on Nov. 12, 2010.

(30) Foreign Application Priority Data

Nov. 13, 2009 (KR) .......... 10-2009-0109946

(51) Int. Cl.
*C07K 7/06* (2006.01)
*A61K 49/00* (2006.01)
*B82Y 5/00* (2011.01)
*A61K 47/48* (2006.01)
*A61K 38/00* (2006.01)

(52) U.S. Cl.
CPC ......... *A61K 49/0002* (2013.01); *A61K 49/0032* (2013.01); *C07K 7/06* (2013.01); *B82Y 5/00* (2013.01); *A61K 49/0056* (2013.01); *A61K 38/00* (2013.01); *A61K 47/48246* (2013.01)
USPC ............. 424/1.69; 424/9.1; 514/1.1; 530/324

(58) Field of Classification Search
None
See application file for complete search history.

(56) References Cited

U.S. PATENT DOCUMENTS

| | | | |
|---|---|---|---|
| 8,217,012 B2 * | 7/2012 | Lee et al. | 514/21.8 |
| 2005/0101524 A1 | 5/2005 | Hogg | |
| 2006/0046271 A1 | 3/2006 | Hallahan | |

OTHER PUBLICATIONS

International Search Report for corresponding International Application No. PCT/KR20101008000, Aug. 31, 2011, 6 pages.

* cited by examiner

*Primary Examiner* — John Ulm
(74) *Attorney, Agent, or Firm* — Edwards Wildman Palmer LLP; Kongsik Kim; Richard B. Emmons (57) ABSTRACT

The present invention relates to a peptide that passes through a blood-brain barrier and binds specifically to apoptotic cells in neurodegenerative brain disease-affected sites, and uses thereof. Therefore, the peptide of the present invention can be used for detecting and imaging apoptotic cells in neurodegenerative brain disease-affected sites, and for targeted drug delivery and theranosis of neurodegenerative brain diseases.

14 Claims, 7 Drawing Sheets

Images taken 2 h after injection of Cy7.5-ApoPep-1

FIG. 3

AD: 13 M-old

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Apoptotic cell-targeting peptide, ApoPep-1

<400> SEQUENCE: 1

Cys Gln Arg Pro Pro Arg
1               5
```

PEPTIDE WHICH PASSES THROUGH BLOOD-BRAIN BARRIER AND TARGETS APOPTOSIS OF NEURODEGENERATIVE BRAIN DISEASE SITE AND USES THEREOF

CROSS-REFERENCE TO RELATED APPLICATIONS

This is a continuation of International Application No. PCT/KR2010/008000 filed on Nov. 12, 2010, which claims the priority to Korean Application No. 10-2009-0109946 filed on Nov. 13, 2009, which applications are incorporated herein be reference.

TECHNICAL FIELD

The present invention relates to a peptide that passes through a blood-brain barrier and targets apoptosis of neurodegenerative brain disease-affected sites and uses thereof. More particularly, the present invention relates to a composition for delivering drugs to brain tissues, a composition for detecting apoptotic cells of neurodegenerative brain disease-affected sites, and a composition for imaging the neurodegenerative brain disease-affected sites which comprises a peptide having an amino acid sequence represented by SEQ ID NO: 1 respectively, and a composition for prevention, treatment, or theranosis of neurodegenerative brain diseases comprising said peptide.

BACKGROUND ART

Apoptosis indicates a phenomenon resulting in the death of unnecessary cells or dangerous cells themselves, which is for life conservation of an individual. In Greek, apoptosis means "to fall." It describes the falling of cell organisms, and was named by comparing the process of cell death to the falling of petals from a flower, which was first observed in 1972 by Kerr, et al (Kerr et al., Br J Cancer, 1972, 26:239-257). Apoptosis plays an important role in physiological events, including cell development, cell differentiation, cellular immunity and the like (Meier et al., Nature, 2000, 407:796-801). Meanwhile, in various pathologic conditions and diseases, apoptosis is important. For example, in neurodegenerative brain diseases such as Alzheimer's disease and Parkinson's disease, due to accumulation of beta amyloid, etc., nerve cells are damaged, thereby increasing apoptosis (Thomson, Science, 1995). As another example, when a successful treatment was performed by an antitumor agent, a large amount of apoptosis is generated in tumor tissues (Thomson, Science, 1995, 267:1456-1462). On the other hand, the reduction of apoptosis is involved in the generation of a tumor. Also, in a stroke and myocardial infarction, due to a lack of blood in the brain and heart, brain cells and myocardium cells are damaged, respectively, resulting in apoptosis (Du et al, J Cereb Blood Flow Metab, 1996, 16:195-201; Narula et al., New Engl J Med, 1996, 335:1182-1189). Also, in diseases such as organ transplantation rejection, autoimmune disease, arteriosclerosis and virus infection, apoptosis frequently occurs (Thomson, Science, 1995, 267:1456-1462; Kageyama et al., Ann Thorac Surg, 1998, 65:1604-1609).

Such apoptosis is very important in clinical diagnosis and treatment. In other words, imaging of apoptosis may be of great help in early diagnosis and progression monitoring of neurodegenerative brain diseases (Alzheimer's disease, Parkinson's disease, etc.), monitoring of disease progression in myocardial infarction and stroke, monitoring of cancer therapeutic effect following antitumor drug treatment, determination on possibility of rupture of atheromatous plaques in arteriosclerosis, or the like, related to excessively increased apoptosis. Also, a selective delivery of a therapeutic or protecting agent to apoptotic cells may significantly improve a therapeutic effect while reducing side effects.

One of the early events occurring in apoptotic cells is the change of the distribution of phospholipids that constitute the cell membrane. The most characteristic thing among them is the exposure of phosphatidylserine to the outside of the cell membrane. Normally, phosphatidylserine is kept inside the cell membrane, but when a cell receives an apoptotic signal or when a red blood cell is aged, it is exposed to the outside of the cell membrane (Fadeel, B. et al., Cell Mol Life Sci, 2003, 60:2575-2585). A macrophage recognizes the exposed phosphatidylserine through a receptor on the cell surface and phagocytoses the apoptotic cell (Fadok, V. A. et al., J immunol 1992, 148:2207-2216; Fadok, V. A. et al., Nature 2000, 405: 85-90; Park, S. Y. et. al., Cell Death Differ, 2008, 15:192-201). Especially, a large number of tumor cells show an increase of expression of phosphatidylserine outside the cell membrane (Utsugi, T. et al., Cancer Res. 1991, 15:3062-3066; Ran, S. et al., Cancer Res. 2002, 62:6132-6140; Woehlecke, H. et al., Biochem J. 2003, 376:489-495). Also, the vascular endothelial cells of a small vessel in a tumor tissue expose phosphatidylserine outside of the cell membrane (Ran, S. et al., Cancer Res. 2002, 62:6132-6140; Zwaal, R. F. A. et al., Blood. 1997, 89:1121-1132). Accordingly, due to such roles of phosphatidylserine, in various situations especially including tumors, the phosphatidylserine is deemed as a target substance for diagnosis, treatment, and treatment monitoring.

At present, the protein annexin V is generally used to detect phosphatidylserine on the surface of apoptotic cells. It is a protein having a molecular weight of 36 kDa, and binds to phosphatidylserine with strong affinity (Vermes, I. et al., Immunol Methods. 1995, 184:39-51). Meanwhile, although annexin V is a very useful target substance or probe for in vitro application, its in vivo application is reported to be restricted because of, for example, slow removal out of the body due to its large molecular weight (Vermeersch, H., et al., Nucl Med Commun. 2004, 25:259-263; Belhocine, T. Z. et al., J Proteome Res. 2004, 3:345-349).

Meanwhile, in the case of Alzheimer's disease, PIB (Pittsburgh Compound B, N-methyl 2-(4'-methylaminophenyl-6-hydroxybenzathiazole) is currently used for nuclear medicine imaging or monitoring, with label of radioisotope [$^{11}$C], because it is combined with beta amyloid protein within Alzheimer's disease-affected tissues. However, whether the accumulation of amyloid exactly reflects nerve injury or apoptosis, and a patient's clinical symptoms is still argued, and not clear. Further, there is a report that [$^{11}$C]-PIB is not a specific imaging probe of Alzheimer's disease, but a non-specific imaging probe of cerebral amyloidosis (beta amyloid-related cerebral amyloidosis) Related to beta amyloid (Lockhart et al., Brain. 2007, 130:2607-2615). In consideration of these views, in a neurodegenerative brain disease such as Alzheimer's disease, it is required to develop a technology for grasping the exact degree of disease progression by directly detecting or diagnosing apoptosis.

Blood-brain barrier (BBB) is a structure having a tight junction between cerebrovascular endothelial cells, and astrocytes strengthening the junction, and inhibits a substance within a blood vessel from passing through a blood vessel wall and reaching the inside of brain parenchyma. For this reason, many drugs developed as brain disease therapeutic agents have a problem in that they cannot easily pass through the blood-brain barrier. Also, materials capable of detecting or targeting apoptosis have a problem in that they cannot easily pass through the blood-brain barrier. At present, the development of a carrier capable of delivering a drug by passing through a blood-brain barrier has been actively conducted. Meanwhile, a peptide having a specific amino acid sequence has a function of delivering a drug or siRNA by passing through a blood-brain barrier (Kumar et al., Nature. 2007, 448:39-43; Teixido and Giralt, Journal of peptide science. 2008, 14:163-173).

Theranosis (theragnosis, theragnostics) is a compound word of therapy with diagnosis (diagnostics), which indicates a therapy technique combined with a diagnosis technique. In such a case, a response in a therapeutic agent for each patient may be determined and applied to selection of a therapeutic method. This may prevent misuse or abuse of drugs, and highly distribute to improvement of a therapeutic effect. (Frederic P et al., Crit. Care Med, 2009, Vol. 37, No. 1(Suppl.) S50-S58; Haglund E et al. Annals of Biomedical Engineering, Vol. 37, No. 10, 2009, pp. 2048.2063; Ozdemir V et al., Nature Biotechnology, Vol. 24, No. 8, 2006, 942-946)

SUMMARY OF THE DISCLOSURE

Accordingly, the present inventors have worked to develop novel proteins or fragments thereof capable of effectively passing through a blood-brain barrier and specifically and early targeting in vivo apoptotic cells within neurodegenerative brain disease-affected tissues. As a result, they have verified that a peptide having an amino acid sequence represented by SEQ ID NO: 1 can pass through a blood-brain barrier and specifically target apoptotic cells within neurodegenerative brain disease-affected tissues. Based on this finding, they have completed this invention.

Accordingly, an object of the present invention is to provide a peptide that passes through a blood-brain barrier and targets apoptosis of neurodegenerative brain disease-affected sites and uses thereof.

To achieve the above object, the present invention provides a drug delivery composition to brain tissues comprising a peptide having an amino acid sequence represented by SEQ ID NO: 1 as an active ingredient.

To achieve another object, the present invention provides a composition for detecting apoptotic cells in neurodegenerative brain disease-affected sites comprising the peptide of the present invention as an active ingredient.

To achieve still another object, the present invention provides a composition for preventing and treating neurodegenerative brain diseases comprising the peptide of the present invention and a therapeutic agent for neurodegenerative brain diseases combined thereto as an active ingredient.

To achieve still another object, the present invention provides a composition for theranosis of neurodegenerative brain diseases comprising the peptide of the present invention, a therapeutic agent for neurodegenerative brain diseases combined thereto and label substances as an active ingredient.

To achieve still another object, the present invention provides a composition for imaging of neurodegenerative brain diseases comprising the peptide of the present invention as an active ingredient.

To achieve still another object, the present invention provides a drug delivery method comprising the step of administering to a subject in need thereof an effective amount of the peptide of the present invention and an agent combined thereto.

To achieve still another object, the present invention provides use of the peptide of the present invention and an agent combined thereto for preparing an agent for drug delivery to brain tissues.

To achieve still another object, the present invention provides a method for detecting apoptotic cells in neurodegenerative brain disease-affected sites comprising the steps of administering to a subject in need thereof an effective amount of the peptide of the present invention and a detecting the peptide.

To achieve still another object, the present invention provides use of the peptide of the present invention for preparing an agent for detecting apoptotic cells in neurodegenerative brain disease-affected sites.

To achieve still another object, the present invention provides a method for preventing or treating neurodegenerative brain diseases comprising the step of administering to a subject in need thereof an effective amount of the peptide of the present invention and a therapeutic agent for neurodegenerative brain diseases combined thereto.

To achieve still another object, the present invention provides use of the peptide of the present invention and a therapeutic agent for neurodegenerative brain diseases combined thereto for preparing an agent for preventing or treating neurodegenerative brain diseases.

To achieve still another object, the present invention provides a method of theranosis for detecting neurodegenerative brain diseases comprising the step of administering to a subject in need thereof an effective amount of the peptide of the present invention, a therapeutic agent for neurodegenerative brain diseases combined thereto and label substances.

To achieve still another object, the present invention provides use of the peptide of the present invention, a therapeutic agent for neurodegenerative brain diseases combined thereto and label substances for preparing an agent for theranosis of neurodegenerative brain diseases.

To achieve still another object, the present invention provides a method for imaging neurodegenerative brain disease-affected sites comprising the steps of administering to a subject in need thereof an effective amount of the peptide of the present invention, detecting and imaging the peptide.

To achieve still another object, the present invention provides use of the peptide of the present invention for preparing an agent for imaging neurodegenerative brain disease-affected sites.

To achieve still another object, the present invention provides a method for monitoring of effect of a therapeutic agent comprising the steps of administering to a subject in need thereof an effective amount of the peptide having an amino acid represented by SEQ ID NO: 1 and label substances combined thereto simultaneously or sequentially with a therapeutic agent and detecting and imaging the peptide.

To achieve still another object, the present invention provides use of the peptide having an amino acid represented by SEQ ID NO: 1 and label substances combined thereto for preparing an agent for monitoring of effect of a therapeutic agent.

BRIEF DESCRIPTION OF DRAWINGS

FIG. 7 shows images obtained as follows. Through immunofluorescence staining on brain tissues of the control mouse, the Parkinson's disease mouse treated with MPTP, and the Parkinson's disease mouse administered with amantadine (a Parkinson's disease therapeutic agent), the antibody staining of tyrosine hydroxylase (Dopaminergic neuron-specific marker) (red) was obtained (a), and was quantified by numerical values (b). Further, the staining of peptide (green) of SEQ ID NO: 1, labeled with FITC fluorescence, and the TUNEL staining (red) (an apoptosis biomarker) were obtained (c), and were quantified by numerical values (d). * indicates statistical significance (p<0.01), and n indicates the number of animals. Each arrow indicates the points where a peptide and each TUNEL staining correspond to each other. DAPI staining (blue) indicates nucleus (AM: amantadine).

DETAILED DESCRIPTION OF THE DISCLOSURE

Hereafter, the present invention will be described in detail.

Based on the principle that a peptide having an amino acid sequence represented by SEQ ID NO: 1 passes through a blood-brain barrier, the present invention provides a drug delivery composition to brain tissues, which comprises a peptide having the amino acid sequence represented by SEQ ID NO: 1 as an active ingredient, a composition for detecting apoptotic cells of neurodegenerative brain disease-affected sites, and a composition for imaging the neurodegenerative brain disease-affected sites, and the peptide, and a composition combined thereto, treatment, or theranosis of neurodegenerative brain diseases, comprising a neurodegenerative brain disease therapeutic agent as an active ingredient.

The peptide of the present invention is a peptide targeting apoptotic cells (amino acid sequence CQRPPR, named "ApoPep-1"), and is specifically bound to apoptotic cells. The peptide of the present invention may have an amino acid sequence of SEQ ID NO: 1 (CQRPPR), comprise all kinds of peptides, proteins, mimetic peptides, compounds and biomedicines, and have activity capable of specifically binding to apoptotic cells. The peptide of the present invention may be obtained from natural sources, or may be synthesized by using a peptide synthesis method known in the art.

As the peptide of the present invention, a peptide capable of specifically binding to apoptotic cells was selected, which is bound to the cells by specifically recognizing apoptotic tumor cells in a culture, normal epithelial cells and macrophages. Also, the peptide of the present invention targets apoptotic cells within tumor tissues, thereby enabling in vivo imaging and monitoring thereof. Further, the peptide can deliver drugs to target disease-affected sites.

Furthermore, the inventive peptide can easily pass through a blood-brain barrier (BBB), and reach the inside of brain tissues, more specifically, brain parenchyma, brain nerve cells or brain nerve tissues. Accordingly, the inventive peptide can specifically bind to apoptotic cells within brain tissues, and thus can deliver a drug to the apoptotic cells.

Accordingly, the present invention provides a drug delivery composition to brain tissues comprising the peptide having an amino acid represented by SEQ ID NO: 1 as an active ingredient. Furthermore, the present invention provides a drug delivery method to brain tissues comprising the step of administering to a subject in need thereof an effective amount of the peptide having an amino acid represented by SEQ ID NO: 1 and label substances combined thereto. In addition. Furthermore, the present invention provides use of the peptide having an amino acid represented by SEQ ID NO: 1 and label substances combined thereto for preparing a drug delivery agent to brain tissues.

The peptide of the present invention may be used as itself or in the form of covalent bond or non covalent bond with other agents. As used herein, the "effective amount" refers to the amount effective in drug delivery or preventing or treating neurodegenerative brain diseases, and the "subject" refers to mammals, particularly, animals comprising human and it may be cells, tissues, organs originated from animals. The subject may be patient in need of treatment.

In order to confirm the functions of the selected inventive peptide specifically binding to apoptotic cells, the present inventors, through various experiments, found that the inventive peptide can pass through a blood-brain barrier, and can specifically recognize apoptotic cells within neurodegenerative brain disease-affected tissues (or sites), thereby binding to the cells. Also, they found that the inventive peptide targets apoptotic cells within neurodegenerative brain disease-affected tissues, thereby enabling in vivo imaging and monitoring thereof. Accordingly, they found that the inventive peptide can be used for delivering a drug to neurodegenerative brain disease-affected sites, detecting and imaging apoptotic cells within neurodegenerative brain disease tissues, and for prevention, treatment and theranosis of a disease in neurodegenerative brain disease-affected tissues, together with a diagnosis or treatment monitoring medicine, or an additional therapeutic medicine.

More specifically, in an example of the present invention, after a peptide having an amino acid sequence represented by SEQ ID NO: 1 (CQRPPR), labeled with a near infrared fluorescent dye, was intravenously injected, it was determined if the peptide can target Alzheimer's disease-affected brain tissues and conduct in vivo imaging on them in an Alzheimer's disease-affected model mouse over-expressing APP/PS1 protein. As a result, it was found that as the severity of disease became serious according to an increase of age, near infrared fluorescence became stronger. On the other hand, when a control peptide was intravenously injected into an Alzheimer's disease-affected mouse, or the inventive peptide was injected into a normal mouse, fluorescence was hardly observed. Further, through observation of fluorescence on isolated brain tissues, similar results were obtained.

In another example of the present invention, the isolated Alzheimer's disease-affected brain tissues were prepared as frozen sections, and subjected to immunofluorescence staining. Then, the location of the inventive peptide within tissues was observed by a microscope. As a result, the antibody staining of caspase-3 (one of biomarkers of apoptosis) and the inventive peptide were located at the same position. In other words, it was confirmed that the inventive peptide was bound to apoptotic cells within brain tissues. Also, it was found that when alpha-smooth muscle actin (one of biomarkers of blood vessel) was antibody-stained, the inventive peptide was located at brain parenchyma outside the blood vessel. In other words, it was confirmed that the peptide can pass through a blood-brain barrier.

In another example of the present invention, into a Parkinson's disease-affected model mouse treated with a drug for induction of Parkinson's disease, the inventive peptide, labeled with a near infrared fluorescent dye was intravenously injected. Then, it was determined if the peptide can target Parkinson's disease-affected brain tissues, and image them in vivo. As a result, at the brain region of the Parkinson's disease-affected mouse, strong near infrared fluorescence was observed. On the other hand, it was found that when a control peptide was intravenously injected into the Parkinson's disease-affected mouse, or the inventive peptide was injected into a normal mouse, fluorescence was hardly observed. Further, through observation of fluorescence on isolated brain tissues, similar results were obtained.

In conclusion, it was found that the inventive peptide can pass through a blood-brain barrier and specifically bind to apoptotic cells within brain tissues, thereby in vivo recognizing and targeting apoptosis of a neurodegenerative brain disease.

Label substances may be used for identification, tracing, qualification, and imaging of the peptide of the present invention and drugs combined thereto. Namely, the peptide of the present invention linked to a detectable mark (example: covalent bonding or cross-linkage) may be provided. The detectable mark may be a radioactive isotope (example: $^{125}$I, $^{32}$P, or $^{35}$S), chromophore, a luminescent or a fluorescent material (example: FITC, RITC, Fluorescent Protein (Green Fluorescent Protein (GFP); EGFP (Enhanced Green Fluorescent Protein); RFP (Red Fluorescent Protein); DsRed (*Discosoma* sp. red fluorescent protein); CFP (Cyan Fluorescent Protein); CGFP (Cyan Green Fluorescent Protein); YFP (Yellow Fluorescent Protein), Cy3, Cy5 and Cy7.5)), super paramagnetic particles, or ultrasuper paramagnetic particles.

Detection techniques based on labeling are widely known in the art. For example, detections may be made as follows. In a case where a fluorescent material is used as a detectable label, immunofluorescence staining may be employed. For example, the inventive liposome labeled with a fluorescent material may be reacted with a test sample, and unbound or unspecifically bound product may be removed. Then, fluorescence emitted by the liposome may be observed under a fluorescent microscope. Also, in a case where an enzyme is used as a detectable label, absorbance may be measured by a color reaction of a substrate through an enzymatic reaction. In a case where a radioactive material is used, a radiation dose may be measured. Furthermore, the detection result may be imaged using a known imaging technique according to the detectable labels.

Since the peptide of the present invention binds specifically to the apoptotic cells or brain tissues, a drug delivery composition of the present invention is specific to apoptosis related diseases such as Alzheimer's disease, Parkinson's disease, Huntington's disease, Amyotrophic lateral sclerosis, Nieman-Pick disease or stroke. In addition, neurodegenerative brain disease may be Alzheimer's disease, Parkinson's disease, Huntington's disease, Amyotrophic lateral sclerosis, Nieman-Pick disease or stroke. That is, by binding to neurodegenerative brain disease-related sites, a composition of the present invention may be used for identification, tracing, qualification, and imaging the sites or delivery of combined agents to the sites.

Meanwhile, the peptide of the present invention can detect apoptotic cells in case that the sites of them are identified, since it binds specifically to apoptotic cells. Accordingly, the present invention provides a composition for detecting apoptotic cells in neurodegenerative brain disease-related sites. Furthermore, the present invention provides a method for detecting apoptotic cells in neurodegenerative brain disease-affected sites comprising the steps of administering to a subject in need thereof an effective amount of the peptide having an amino acid sequence represented by SEQ ID NO: 1 and detecting the peptide. Also, the present invention provides use of a peptide having an amino acid sequence represented by SEQ ID NO: 1 for preparing an agent for detecting apoptotic cells in neurodegenerative brain disease-affected sites.

The peptide of the present invention is capable of specifically binding to apoptotic cells in neurodegenerative brain disease-affected tissues, and thus may be used as an intelligent drug carrier for selectively delivering an agent to the cells. Accordingly, the present invention provides a drug delivery composition for treating a neurodegenerative brain disease comprising the peptide of the present invention as an active ingredient.

In a case where the peptide of the present invention comprised in the drug delivery composition of the present invention is used for treatment in connection with a conventional nerve cell protecting agent or a conventional brain neurological disease therapeutic agent, since the medicine is selectively delivered to only apoptotic cells by the peptide of the present invention, it is possible to increase the efficacy of the drug, and at the same time to significantly reduce the side effects on normal cells.

Meanwhile, the present invention provides a composition for preventing and treating neurodegenerative brain diseases comprising the peptide of the present invention and a therapeutic agent for neurodegenerative brain diseases combined thereto as an active ingredient. In addition, the present invention provides a method for preventing and treating neurodegenerative brain diseases comprising the step of administering to a subject in need thereof an effective amount of the peptide having an amino acid sequence represented by SEQ ID NO: 1 and a therapeutic agent for neurodegenerative brain diseases combined thereto. Also the present invention provides use of the peptide having an amino acid sequence represented by SEQ ID NO: 1 and a therapeutic agent for neurodegenerative brain diseases combined thereto for preparing an agent for preventing and treating neurodegenerative brain diseases.

In addition, the present invention provides a composition for theranosis of neurodegenerative brain diseases comprising the peptide having an amino acid sequence represented by SEQ ID NO: 1, a therapeutic agent for neurodegenerative brain diseases combined thereto and label substances as an active ingredient. In addition, the present invention provides a method for theranosis of neurodegenerative brain diseases comprising the step of administering to a subject in need thereof an effective amount of the peptide having an amino acid sequence represented by SEQ ID NO: 1, a therapeutic agent for neurodegenerative brain diseases combined thereto and label substances. Also the present invention provides use of the peptide having an amino acid sequence represented by SEQ ID NO: 1 a therapeutic agent for neurodegenerative brain diseases combined thereto and label substances for preparing an agent for theranosis of neurodegenerative brain diseases.

There is no limitation in the neurodegenerative brain disease therapeutic agent to be connection with the inventive peptide as long as it has been conventionally used for the treatment of the disease. For example, brain nerve cell protecting agents (such as NMDA (N-methyl-d-aspartate) receptor inhibitor, acetylcholine esterase inhibitor, anti-amyloid protein agent), e.g., Donepezil, galanthamine, Tacrine, memantine, etc, may be used. The medicine may be connected with the peptide of present invention by a method known in the art, e.g., a covalent bond, a crosslinking bond, etc. For this, the peptide of the present invention, as required, may be chemically modified within a range where its activity is not lost. The amount of the peptide of the present invention to be comprised in the composition of the present invention may vary according to the kind and amount of the therapeutic agent to be connected with the peptide.

The compositions of the present invention may be a pharmaceutical composition and it may be provided as a pure form of the peptide, an agent or medicine, label substances or their combination or a formulated form with a pharmacologically acceptable carrier. 'Pharmacologically acceptable' means a non-toxic composition which does not produce an allergic or a similar reaction such as a stomach disorder or vertigo when the composition is physiologically permissible and medicated to human. The carrier is all kinds of solvent, a dispersion medium, an o/w or w/o emulsion, an aqueous composition, liposome, a microbead, a microsome and biodegradable nanoparticle. Preferably, the pharmaceutical compositions of the present invention may comprise 0.001~99.999 weight % of pharmacologically acceptable carriers.

Also, the composition of the present invention may comprise 0.00001%~20% of small molecules of the peptide of the present invention and 80~99.99999 weight % of pharmacologically acceptable carriers. Also, the present invention may comprise 0.00001%~20 weight % of the peptide of the present invention, for example, 0.00001%~20 weight % of a therapeutic agent for neurodegenerative brain diseases, and 60~99.99998 weight %, that is the remaining, of the pharmacologically acceptable carrier. In addition, a composition of the present invention may further comprise 0.00001~20 weight % of label substances (In this case, the amount of the carrier is reduced).

Meanwhile, the pharmacological compositions may be formulated with a proper carrier according to a medication route. The medication route according to the present invention is an oral or parenteral route, but not limited thereto. The parenteral medication route contains a transdermal, a nasal cavity, an abdominal cavity, a muscle, a hyperdomic, or a vein.

In case of the oral administration of the pharmacological composition of the present invention, it can be formulated in the form of powder, granule, tablets, pills, sugar coated tablets, capsules, fluids, gels, syrups, suspensions wafers, and the like. Example of a proper carrier may comprise a series of saccharide such as lactose, dextrose, sucrose, sorbitol, mannitol, xylitol, erythritol, and maltitol; a series of starch such as corn starch, wheat starch, rice starch, and potato starch; a series of cellulose such as cellulose, methyl cellulose, sodium carboxy methyl cellulose, and hydroxyl propylmethyl cellulose; and a series of filler such as gelatin and polyvinyl pyrrolidone. In some cases, a disintegrants such as cross-linked polyvinyl pyrrolidone, agar, alginic acid, or sodium alginate may be added. The pharmacological compositions may additionally contain a flocculant, a lubricant, a wetting agent, a perfume, an emulsifying agent, or a preservative.

When the pharmacological compositions are used for parenteral administration, the pharmacological composition may be formulated by a known method in the form of an injections, transdermal preparations, and nasal preparation with a proper carrier. The injections have to be sterilized and prevented from microorganism contaminations such as bacteria or fungus. In the case of a injections, the proper carrier is, but not limited thereto, water, ethanol, polyol (example; glycerol, propylene glycol, liquid polyethylene glycol), or a mixture of the above materials and/or a solvent or a dispersion medium containing a vegetable oil. More preferably, the proper carrier is hanks solution, linger solution, phosphate buffered saline containing triethanol amine, a sterilized solution for a injections, or a isotonic solution such as 10% ethanol, 40% propylene glycol, or 5% dextrose. Antimicrobial or antifungal such as paraben, chloro butanol, phenol, sorbic acid, and thimerosal may be added for the prevention of the injections from microorganism contaminations. And, the most of injections may contain an isotonic agent such as sugar or sodium chloride. Those formulations are described in an existing formula known to the pharmaceutical chemistry (*Remington's Pharmaceutical Science*, 15th Edition, 1975, Mack Publishing Company, Easton, Pa.).

In the case of a nasal preparation, the compounds used in the present invention are easily delivered in the form of aerosol spray from a pressurized pack or a nebulizer. For the production of a nasal preparation, the proper propellant such as dichlorofluoro methane, trichlorofluoro methane, dichlorotetrafluoro ethane, carbon dioxide, or the other proper gas is used. In the case of pressurized aerosol, a dosage unit is determined by a valve delivering a measured quantity. For instance, a gelatin capsule or a cartridge used in an inhaler or an insufflator may be formulated to contain a powder base such as lactose or starch.

The other pharmaceutically acceptable carriers may be referred from the below-mentioned literature (Remington's Pharmaceutical Sciences, 19th ed., Mack Publishing Company, Easton, Pa., 1995).

Furthermore, the pharmacological compositions according to the present invention may additionally contain one or more buffer (example; NaCl solution or PBS), a carbohydrate (example; glucose, mannose, sucrose, or dextran), a stabilizer (example; sodium bisulfate, sodium sulfite, or ascorbic acid), an antioxidant, a bacteriostat, a chelating agent (example; EDTA or glutathione), an adjuvant (example; aluminum hydroxide), a suspension agent, a thickener, and/or a preservative (example; benzalkonium chloride, methyl or propylparaben, or chlorobutanol).

Also, the pharmaceutical composition of the present invention may be formulated by using the method known in the art so that it can provide rapid, continuous or delayed release of an active ingredient after it is administered to a mammalian.

An effective amount of the pharmacological compositions formulated by the above methods are administered to a number of routes such as oral, transdermal, hypodermic, vein, or muscle. Here, 'effective amount' means an amount of a compound or an extract which makes it possible to trace a treatment effect or diagnosis when the pharmacological composition is medicated to a patient. A dosage of the pharmacological composition according to the present invention is selected by a administration route, a administering subject, a type and a degree of a serious illness of a disease, an age, sex and body weight, individual differences, and a disease condition. Preferably, the content of an active ingredient in the pharmacological composition of the present invention may be varied by a disease condition, and I may be administered with an effective amount in a dosage of several times a day.

Moreover, the peptide of the present invention is specifically bound to apoptotic cells in neurodegenerative brain tissues, and thus it may be useful for imaging and diagnosis of the lesion thereof. Accordingly, the present invention provides a method for imaging neurodegenerative brain disease-affected sites comprising the steps of administering to a subject in need thereof an effective amount of the peptide having an amino acid sequence represented by SEQ ID NO: 1, detecting and imaging the peptide. In addition, the present invention provides use of the peptide having an amino acid sequence represented by SEQ ID NO: 1 for preparing an agent for imaging neurodegenerative brain disease-affected sites.

At this time, imaging and diagnosis of neurodegenerative brain diseases are, not limited thereto, used for monitoring of the progress of diseases, the result of treatment, reaction against therapeutic agent as well as the first medical examination.

Accordingly, the composition of the present invention may be used for theranosis (theragnosis, theranostics).

The present invention provides a method for monitoring of the therapeutic agent effect comprising the steps of administering to a subject in need thereof an effective amount of a peptide having an amino acid sequence represented by SEQ ID NO: 1 and label substances thereto concurrently or sequentially and detecting and imaging the peptide.

Also, the present invention provides uses of a peptide having an amino acid sequence represented by SEQ ID NO: 1 and label substances for preparing an agent for monitoring effect of a therapeutic agent.

The therapeutic agent may be a therapeutic agent for neurodegenerative brain disease. The therapeutic agent, and the peptide of the present invention covalently or non-covalently bonded to a labeling material may be concurrently or sequentially administered to a subject. The sequential administration refers to that the therapeutic agent, the peptide of the present invention, and label substances thereto are sequentially administered with a predetermined interval, irrespective of administration order.

The monitoring of the therapeutic agent effect may be useful in theranosis such as monitoring of disease progression, treatment, response to the therapeutic agent.

Techniques for nucleotides and proteins of the present invention may be referred to the following literatures: Maniatis et al., *Molecular Cloning: A Laboratory Manual*, Cold Spring Harbor Laboratory 1982; Sambrook et al., *Molecular Cloning; A Laboratory Manual*, Cold Spring Harbor Press, N.Y., Second (1998) and Third (2000) Editions; *Gene Expression Technology, Method in Enzymology, Genetics and Molecular Biology, Method in Enzymology*, Guthrie & Fink (eds.), Academic Press, San Diego, Calif. 1991; and Hitzeman et al., *J. Biol. Chem.*, 255, 12073-12080 1990.

As can be seen foregoing, a peptide having an amino acid sequence represented by SEQ ID NO: 1 of the present invention can pass through a blood-brain barrier and can bind specifically to apoptotic cells in neurodegenerative brain disease-affected sites. Therefore, the peptide of the present invention can be used for detecting apoptosis in neurodegenerative brain diseases and further detecting apoptotic cells (especially apoptotic neuronal cells) in neurodegenerative brain disease-affected sites and imaging, targeted drug delivery, theranosis.

EXAMPLES

Hereinafter, the present invention will be described in detail with reference to Examples.

However, Examples below are for illustrative purposes only and are not constructed to limit the scope of the present invention.

Example 1

In Vivo Imaging of Alzheimer's Disease Using the Inventive Peptide

<1-1> In Vivo Imaging of Alzheimer's Disease Using the Inventive Peptide

As an Alzheimer's disease model, a transgenic mouse model over-expressing Amyloid precursor protein (APP) gene and Presenilin 1 (PS1) gene was used. The model animal has a characteristic that apoptosis together with extracellular accumulation of beta amyloid protein (one of the characteristics of Alzheimer's disease) gradually increases according to an increase of age. On mice, from a 5 month old mouse (early stage of alzheimer's disease) to a 13 month old mouse (severe stage), this experiment was performed according to the progression of disease. The apoptosis was confirmed by TUNEL (in vitro terminal deoxynucleotidyl transferase-mediated dUTP nick-end labeling) assay according to the manufacturer (Roche)'s instructions. In this method, biotin-dUTP is labeled at the end of a cleaved DNA fragment specifically occurring in apoptosis by using terminal deoxynucleotidyl transferase enzyme, and then fluorescence staining is performed by streptavidin-rhodamine (red fluorescent dye).

Figure 1:
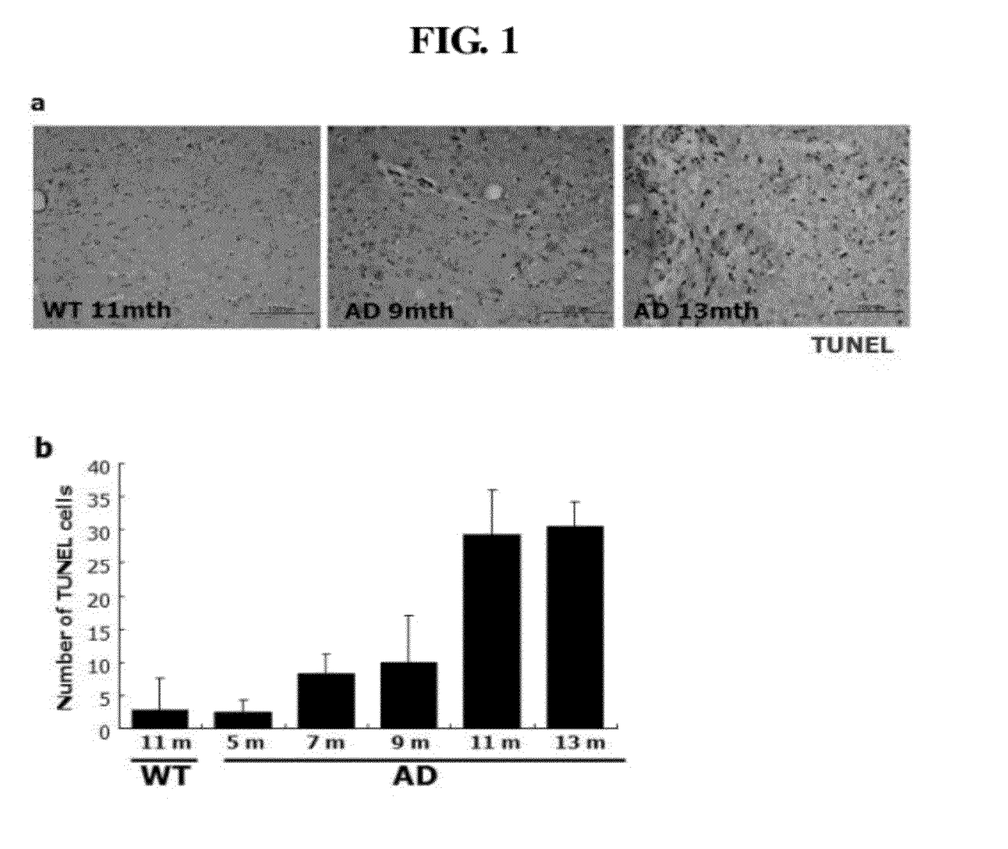
FIG. 1 shows an increase of apoptosis observed by TUNEL staining together with extracellular accumulation of beta amyloid protein (one of the characteristics of Alzheimer's disease) according to an increase of age of a mouse, from a 5 month old mouse (early stage of Alzheimer's disease) to a 13 month old mouse (severe stage). A control is a normal mouse which was born from the same parent as an Alzheimer's disease-affected mouse.

As a result, as shown in FIG. 1, it was confirmed that as compared to a 9 month old mouse, a 13 month old mouse showed more TUNEL-stained cells, that is, more apoptotic cells (see FIG. 1a). On the other hand, a control mouse, even an 11 month old mouse, hardly showed TUNEL-stained cells.

The control mouse is a normal mouse which was born from the same parent as an Alzheimer's disease-affected mouse. Also, when on 5, 7, 9, 11, and 13 month old mice, the number of TUNEL-stained cells according to disease progression was analyzed, it was found that apoptosis was increased in proportion to disease progression (see FIG. 1b).

The Alzheimer's disease-affected mouse (5, 7, 9, and old) models were intravenously injected with the inventive peptide (ApoPep-1) labeled with Cy7.5 near infrared fluorescence, under isoflurane anesthesia, to a final concentration of 50 μM. After 2 hours from the injection, a head region was imaged by near infrared imaging, and each brain was isolated and imaged by near infrared imaging. An in vivo near infrared fluorescence image was imaged by an Optix exPlore machine (ART). Also, by using the machine's own software, each image was standardized.

The peptide used in the present invention was synthesized by a standard Fmoc method, and separated by HPLC machine. The synthesis of the peptide was carried out by special companies (Peptron and Anygen). The peptide was synthesized in such a manner that N-terminal was combined with fluorescein isothiacyanate (FITC). Otherwise, after the synthesis of the peptide, N-terminal was combined with Cy7.5 near infrared fluorescent dye.

Figure 2:
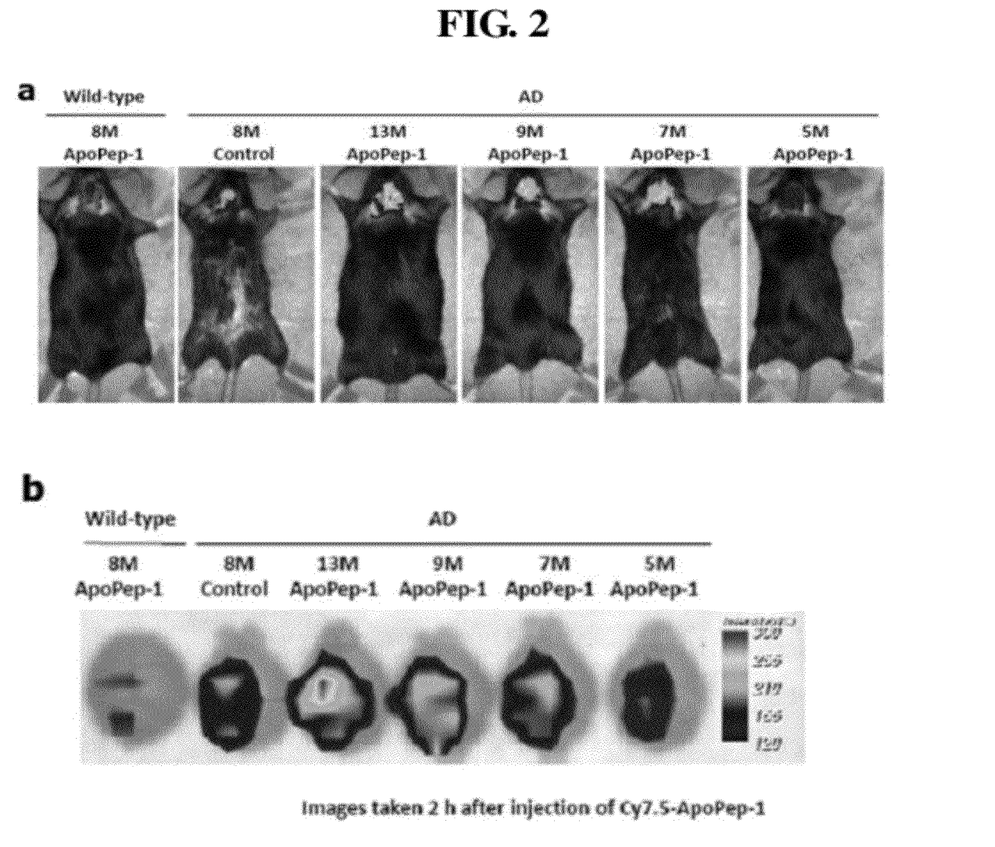
FIG. 2 shows images obtained as follows. Into Alzheimer's disease-affected mouse (5, 7, 9, and 13 months old) models, a peptide (ApoPep-1) of SEQ ID NO: 1, labeled with Cy7.5 near infrared fluorescence, was intravenously injected. After 2 hours from the injection, a head region was imaged by near infrared imaging (a), and each brain was isolated and imaged by near infrared imaging (b). Also, after injection of a control peptide into an Alzheimer's disease-affected mouse (8 months old), and injection of a peptide of SEQ ID NO: 1 into a normal (wild type) mouse (8 months old), the mice were imaged in the same conditions as those above.

As a result, as shown in FIG. 2a, it was observed that as Alzheimer's disease became serious (increase of apoptosis of nerve cells), the near infrared fluorescence intensity level increased. Meanwhile, when a control peptide (amino acid sequence, NSSSVDK) was applied to an Alzheimer's disease-affected mouse (8 months old), near infrared fluorescence was hardly observed. Also, when a normal (wild type) mouse (8 months old) was injected with the inventive peptide, it was observed that an Alzheimer's disease-affected mouse (similar age, 7 and 9 months old) showed a much stronger near infrared fluorescence at the brain region than the normal mouse.

Also, as shown in FIG. 2b, on each isolated brain, when fluorescence measurement in vitro was carried out, the similar result as that in the in vivo imaging was obtained.

<1-2> Immunofluorescence Staining Analysis of Alzheimer's Disease-Affected Brain Tissues Injected with the Inventive Peptide For histological examination, the brain tissues isolated from the mouse (13 months old) injected with the inventive peptide labeled with FITC fluorescence (green), which had been subjected to in vivo imaging in Example <1-1>, were postfixed by 4% paraformaldehyde liquid, and immersed in Sucrose/phosphate buffer for 24 hours. Then, they were prepared as frozen sections with a thickness of 30 μm by cryostat. Immunofluorescence staining on an antibody was carried out by using a secondary antibody labeled with alexa 568 (red fluorescent dye). Each tissue slide was observed by a fluorescence microscope (Zeiss).

Figure 3:
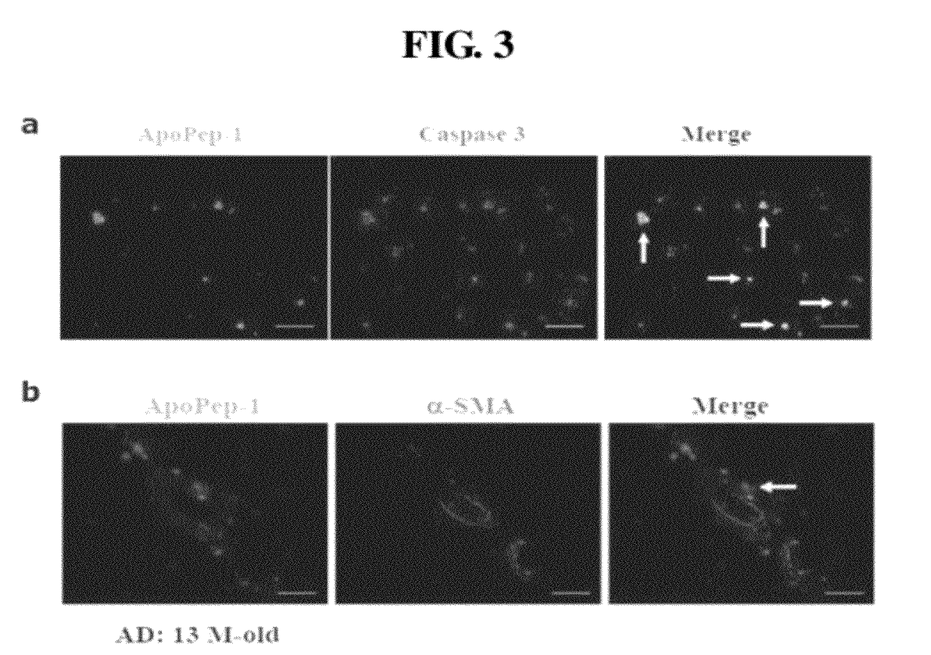
FIG. 3 shows images obtained as follows. Through immunofluorescence staining on brain tissues of an Alzheimer's disease-affected mouse, the staining of peptide (green) of SEQ ID NO: 1, labeled with FITC fluorescence, and the antibody staining (red) of Caspase-3 (an apoptosis biomarker) were obtained (a). Further, blood vessel staining within the brain tissues was performed, in which the antibody staining (red) of α-SMA was obtained (b). Each arrow indicates the points where a peptide and each antibody staining correspond to each other.

As a result, as shown in FIG. 3, it was confirmed that the inventive peptide (green fluorescence) and the antibody (red fluorescence) to Caspase-3 (apoptosis biomarker) were concurrently stained at the same cell (see FIG. 3a). This indicates that the inventive peptide targets apoptotic cells.

Also, as shown in FIG. 3b, through blood vessel staining within brain tissues, that is, the antibody staining (red fluorescence) of alpha-smooth muscle actin (α-SMA), it was observed that the inventive peptide is distributed within brain parenchyma outside of a brain blood vessel by passing through the brain blood vessel.

Example 2

In Vivo Imaging of Parkinson's Disease Using the Inventive Peptide

Parkinson's disease was induced by specifically destroying a dopaminergic neuron existing in substantia nigra of a brain by a drug. For this, to each of C57BL male mice (koatech) (body weight: 21 to 23 g), MPTP (1-methyl-4-phenyl-1,2,3,6-tetrahydro pyridine hydrochloride) (Sigma) was administered with a single dose of 15 mg/kg. MPTP administration was carried out with an interval of 2 hours, four times through intraperitoneal injection, and each mouse was administered with MPTP in a total amount of 60 mg/kg.

On day 7, 14, and 21 from the administration of MPTP (day 0), the inventive peptide labeled with Cy7.5 was injected. The peptide was intravenously injected into a tail vein to a final concentration of 50 μM, under isoflurane anesthesia, and was circulated for 2 hours. Then, an in vivo near infrared fluorescence image was imaged. The mouse on which the experiment had been completed was immediately subjected to anesthesia and euthanasia. Then, a brain tissue sample was collected. From the dead mouse, blood was immediately removed by saline solution flushing through heart, and primarily fixed by re-flushing of 4% paraformaldehyde solution. The primarily fixed brain was collected from the mouse, and then postfixed by being placed for 1 day in 30% sucrose/phosphate buffer solution, and placed for 1 day in 4% paraformaldehyde phosphate buffer solution. The fixed brain tissues were rapidly frozen by dry ice, and formed into a block for frozen fractions. At some desired time, the stored brain block was prepared as frozen fractions, and used for various staining methods.

Also, in order to monitor the therapeutic effect of a drug, after 30 minutes from the administration of MPTP, amantadine used as a Parkinson's disease therapeutic agent was intraperitoneally administered into each mouse in a dose of 25 mg/kg a total of seven times with a one day interval. On day 7 from the administration of amantadine, the inventive peptide labeled with Cy7.5 was injected, and imaging and tissue staining were carried out in the same manner as described above. Apoptosis was analyzed in the same manner as described in Example <1-1>.

Figure 4:
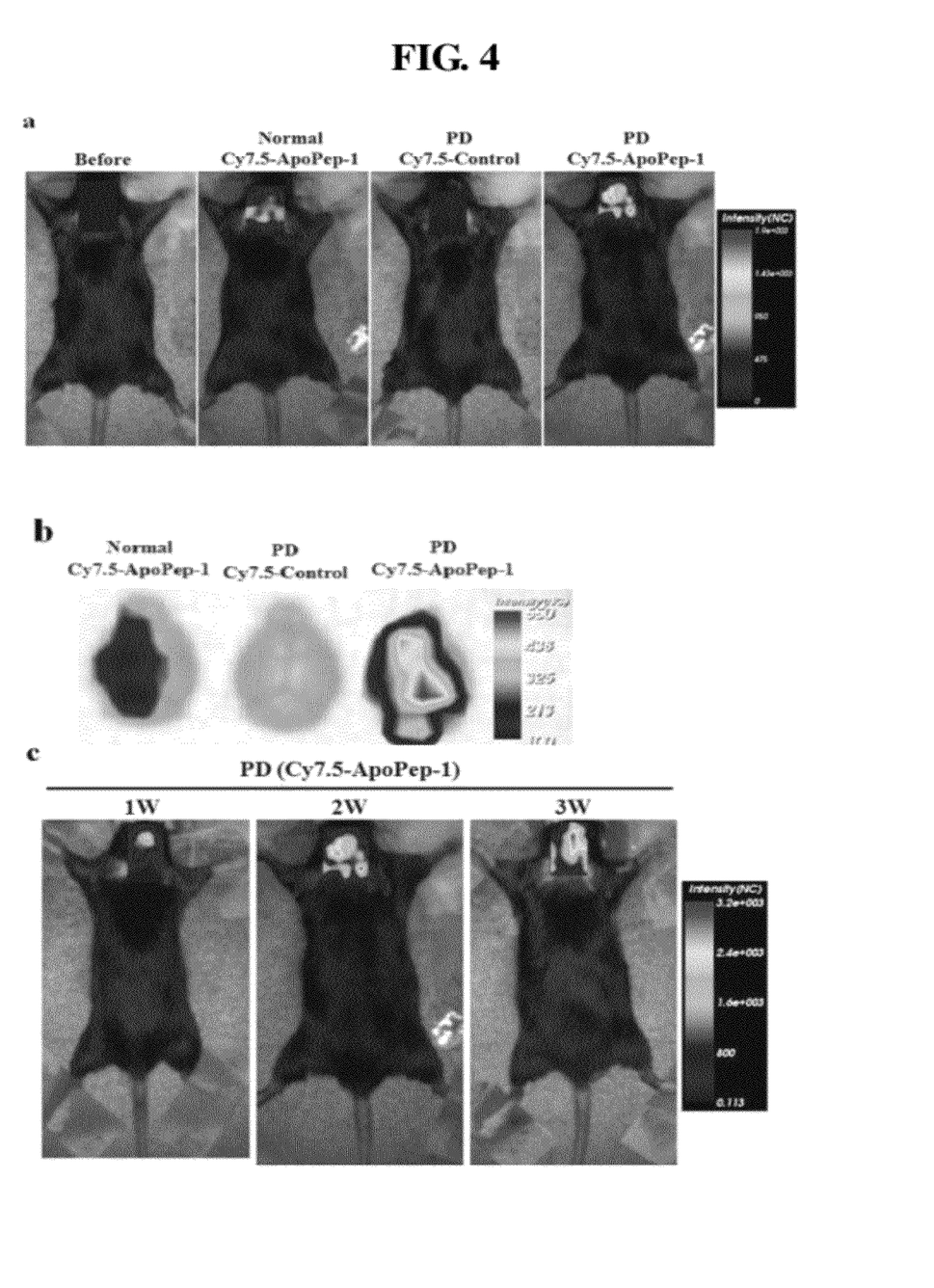
FIG. 4 shows images obtained as follows. Into Parkinson's disease-affected mouse models, a peptide (ApoPep-1) of SEQ ID NO: 1, labeled with Cy7.5 near infrared fluorescence, was intravenously injected. After 2 hours from the injection, a head region was imaged by near infrared imaging (a), and each brain was isolated and imaged by near infrared imaging (b). Also, after injection of a control peptide into a Parkinson's disease-affected mouse, and injection of a peptide of SEQ ID NO: 1 into a normal mouse, the mice were imaged in the same conditions as those above. Further, after 1, 2, and 3 weeks from the induction of Parkinson's disease, the mice were injected with peptide of SEQ ID NO: 1, and imaged (c) in the same manner as FIG. 4(a).

As a result, as shown in FIG. 4a, when into the Parkinson's disease-affected mouse, the inventive peptide was injected, strong near infrared fluorescence was observed at the brain region. On the other hand, in the case of the control peptide, near infrared fluorescence was hardly observed. Also, when into the normal (wild type) mouse, the inventive peptide was injected, near infrared fluorescence was hardly observed.

Also, as shown in FIG. 4b, when each brain was isolated and its near infrared fluorescence was measured in vitro, the similar results as those in in vivo imaging were obtained.

Also, as shown in FIG. 4c, it was observed that with the lapse of time (after 1 week, 2 weeks, and 3 weeks from administration of MPTP), near infrared fluorescence at a brain region became stronger.

Figure 5:
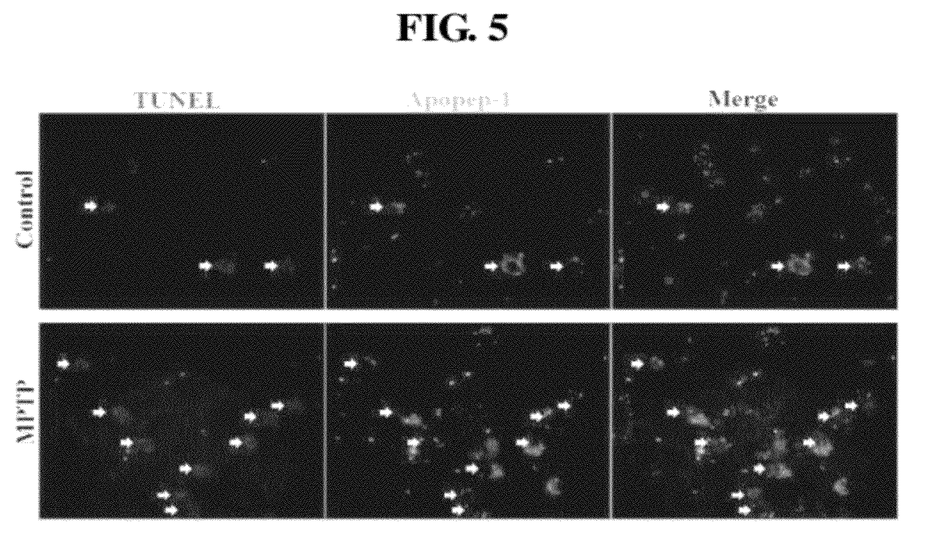
FIG. 5 shows images obtained as follows. Through immunofluorescence staining on brain tissues of a control mouse, and a Parkinson's disease-affected mouse treated with MPTP, the staining of peptide (green) of SEQ ID NO: 1, labeled with FITC fluorescence, and the TUNEL staining (red) (an apoptosis biomarker) were obtained. Each arrow indicates the points where a peptide and each TUNEL staining correspond to each other. DAPI staining (blue) indicates a nucleus.

Also, as shown in FIG. 5, it was confirmed that the inventive peptide (green fluorescence) and TUNEL staining (red fluorescence) (apoptosis biomarker) were concurrently located at the same cell. This indicates that the inventive peptide targets apoptotic cells.

Figure 6:
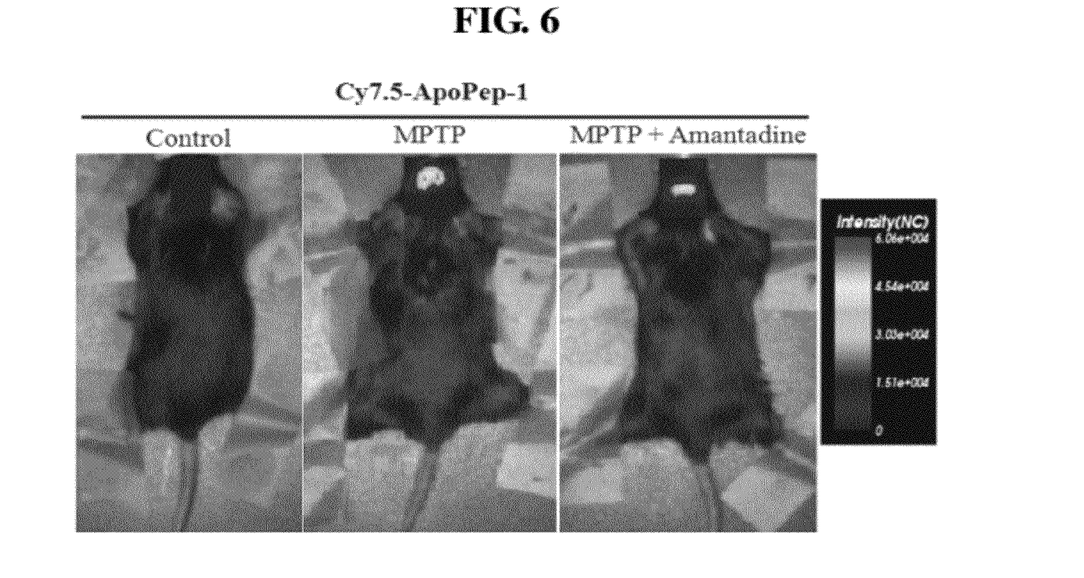
FIG. 6 shows images obtained as follows. Into a control mouse, a Parkinson's disease-affected mouse treated with MPTP, and a Parkinson's disease-affected mouse administered with amantadine (a Parkinson's disease therapeutic agent), a peptide of SEQ ID NO: 1 was injected. Then, the mice were imaged in the same manner as FIG. 5.

Also, as shown in FIG. 6, it was observed that the mouse administered with amantadine following MPTP showed a lower near infrared fluorescence than the mouse administered with MPTP. This indicates that a drug therapeutic effect can be monitored by the inventive peptide.

Figure 7:
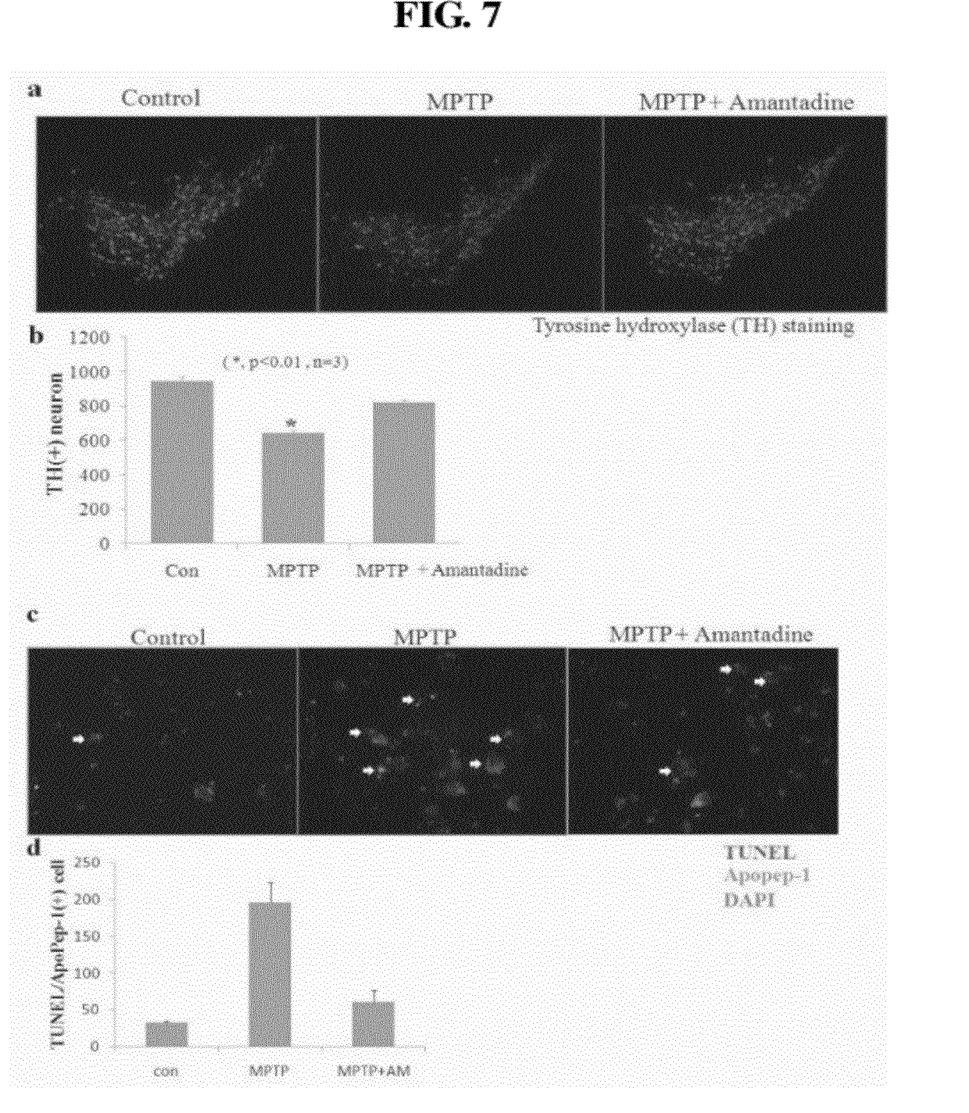

Also, as shown in FIG. 7a, it was observed that unlike the mouse administered with MPTP, the mouse administered with amantadine following MPTP showed an increase of antibody staining of tyrosine hydroxylase (TH) (a dopaminergic neuron-specific marker). FIG. 7b shows the quantified result of the number of TH-stained dopaminergic neurons of FIG. 7a. This indicates that the number of neurons statistically significantly increased due to the therapeutic effect of a drug (p<0.01).

Also, as shown in FIG. 7c, it was observed that unlike the mouse administered with MPTP, the mouse administered with amantadine following MPTP showed a decrease of TUNEL staining (red fluorescence) (apoptosis biomarker). Also, it was confirmed that the inventive peptide (green fluorescence) and TUNEL staining were located at the same cell. FIG. 7d shows the quantified result of the number of TUNEL-stained apoptotic cells of FIG. 7c. This indicates a reduction of apoptosis in neurons due to the therapeutic effect of a drug.

Although a preferred embodiment of the present invention has been described for illustrative purposes, those skilled in the art will appreciate that various modifications, additions and substitutions are possible, without departing from the scope and spirit of the invention as disclosed in the accompanying claims.

As can be seen foregoing, a peptide having an amino acid sequence represented by SEQ ID: No. 1 of the present invention can pass through a blood-brain barrier and can bind specifically to apoptotic cells in neurodegenerative brain disease-affected sites. Therefore, the peptide of the present invention can be used for detecting apoptosis in neurodegenerative brain diseases and further detecting apoptotic cells (especially apoptotic neuronal cells) in neurodegenerative brain disease-affected sites and imaging, targeted drug delivery, theranosis.

4. A composition for detecting apoptotic cells in neurodegenerative brain disease-affected sites comprising a peptide having an amino acid sequence represented by SEQ ID NO: 1 as an active ingredient.

5. A composition for treating a neurodegenerative brain disease comprising a peptide having an amino acid sequence represented by SEQ ID NO: 1 and a therapeutic agent for neurodegenerative brain diseases combined thereto as an active ingredient.

6. The composition of claim 5, wherein the neurodegenerative brain disease is selected from the group consisting of Alzheimer's disease, Parkinson's disease, Huntington's disease, Amyotrophic lateral sclerosis, Nieman-Pick disease and stroke.

7. A composition for theranosis of neurodegenerative brain diseases comprising the peptide of a peptide having an amino acid sequence represented by SEQ ID NO: 1, a therapeutic agent for neurodegenerative brain diseases combined thereto and label substances as an active ingredient.

8. A composition for imaging of neurodegenerative brain diseases-affected sites comprising a peptide having an amino acid sequence represented by SEQ ID NO: 1 as an active ingredient.

9. A drug delivery method comprising the step of administering to a subject in need thereof an effective amount of a peptide having an amino acid sequence represented by SEQ ID NO: 1 and a therapeutic agent for neurodegenerative brain diseases combined thereto.

10. A method for detecting apoptotic cells in neurodegenerative brain disease-affected sites comprising the steps of administering to a subject in need thereof an effective amount of a peptide having an amino acid sequence represented by SEQ ID NO: 1 and detecting the peptide.

The invention claimed is:

1. A drug delivery composition to brain tissues comprising a peptide having an amino acid sequence represented by SEQ ID NO: 1 as an active ingredient.

2. The composition of claim 1, wherein the peptide is labeled with anyone selected from the group consisting of chromogenic enzyme, radioactive isotope, chromophore, a luminescent material, fluorescer, super paramagnetic particles, and ultrasuper paramagnetic particles.

3. The composition of claim 1, wherein the drug delivery composition is used for targeting a disease selected from the group consisting of Alzheimer's disease, Parkinson's disease, Huntington's disease, Amyotrophic lateral sclerosis, Nieman-Pick disease and stroke.

11. A method for treating neurodegenerative brain diseases comprising the step of administering to a subject in need thereof an effective amount of a peptide having an amino acid sequence represented by SEQ ID NO: 1 and a therapeutic agent for neurodegenerative brain diseases combined thereto.

12. A method of theranosis for neurodegenerative brain diseases comprising the step of administering to a subject in need thereof an effective amount of a peptide having an amino acid sequence represented by SEQ ID NO: 1, a therapeutic agent for neurodegenerative brain diseases combined thereto and label substances.

13. A method for imaging neurodegenerative brain disease-affected sites comprising the steps of administering to a subject in need thereof an effective amount of a peptide having an amino acid sequence represented by SEQ ID NO: 1, detecting and imaging the peptide.

14. A method for monitoring the effect of a therapeutic agent comprising the steps of administering to a subject in need thereof an effective amount of a peptide having an amino acid represented by SEQ ID NO: 1 and label substances combined thereto simultaneously or sequentially with a therapeutic agent and detecting and imaging the peptide.

* * * * *